United States Patent [19]

Berninger

[11] 4,446,237

[45] May 1, 1984

[54] METHOD FOR DETECTION OF A SUSPECT VIRAL DEOXYRIBONUCLEIC ACID IN AN ACELLULAR BIOLOGICAL FLUID

[75] Inventor: Mark S. Berninger, Gaithersburg, Md.

[73] Assignee: Life Technologies, Inc., Chagrin Falls, Ohio

[21] Appl. No.: 248,048

[22] Filed: Mar. 27, 1981

[51] Int. Cl.$^3$ ............... G01N 33/58; G01N 33/60; C12N 15/00
[52] U.S. Cl. ............................. 436/504; 435/5; 435/6
[58] Field of Search ............... 424/11, 12; 23/230 B; 436/504; 435/172

[56] References Cited

U.S. PATENT DOCUMENTS

| | | | |
|---|---|---|---|
| 4,000,252 | 12/1976 | Kosak | 424/1 |
| 4,048,298 | 9/1977 | Niswender | 424/1 |
| 4,066,512 | 1/1978 | Lai et al. | 195/127 |
| 4,139,346 | 2/1979 | Rabbani | 436/504 |
| 4,302,204 | 11/1981 | Wahl et al. | 424/1.5 |
| 4,358,535 | 11/1982 | Falkow et al. | 435/5 |

FOREIGN PATENT DOCUMENTS 2034323 6/1980 United Kingdom ............... 435/172

OTHER PUBLICATIONS

Moseley et al., J. Infectious Diseases, 142 (1980) 892–898.
Gillespie et al., Chem. Abstracts, 63 (1965) #8647d.
Slor, Chemical Abstracts, vol. 83 (1975) abstract #23985c.

Primary Examiner—Christine M. Nucker
Attorney, Agent, or Firm—Louis E. Marn; Paul H. Kochanski; Elliot M. Olstein

[57] ABSTRACT

There is disclosed a method for evaluating acellular biological fluid for viral DNA, such as DNA of the Hepatitus-B virus, whereby the acellular biological fluid is treated to immobilize in denatured form the DNAs including the suspect viral DNA on a solid support or substrate with the resulting solid substrate being contacted with a solution including radioisotropically-labeled viral denatured DNA followed by analysis of solid substrate for radioisotopically-labeled suspect viral renatured DNA.

20 Claims, No Drawings

METHOD FOR DETECTION OF A SUSPECT VIRAL DEOXYRIBONUCLEIC ACID IN AN ACELLULAR BIOLOGICAL FLUID

FIELD OF THE INVENTION

This invention relates to a method of detection of a suspect viral deoxyribonucleic acid, and more particularly to the detection of a suspect viral deoxyribonucleic acid (hereinafter sometimes referred to as "DNA") in an acellular biological fluid, such as human serum, cerebral spinal fluid and the like.

BACKGROUND OF THE INVENTION

Methods or protocols for the detection and quantitation of specific nucleic acid sequences including nucleic acid purification, denaturation and the like are well known in the field of research molecular biology. Much of the work in the field of thermal renaturation of DNA has been performed by Marmur and Doty, (1961) *J. Mol. Biol.* 3, 585 wherein comparisons are made between DNA and renatured DNA showing the reproducibility of the helix-coil transition and the reformation of the same secondary structure.

A technique for the immobilization of denatured DNA to a solid substrate, such as a nitrocellulose filter, and subsequent renaturation or hybridization by a complimentary RNA has been reported by Gillespie and Siegelman (19-5), *J. Mol. Biol.* 12, 829. Such technique was further modified and extended by Denhardt, (1966) *Biochemical and Biophysical Research Communications* 23, No. 5, 641, to detect complimentary denatured DNA sequences with the use of a labeled DNA probe. A method for the detection of Epstein-Barr viral DNA in lymphoid cell lines is disclosed by Braudsma and Miller, (1980) *Proc. Natl. Acad. Sci. U.S.A.*

One clinical method available to determine infectivity of a suspect human serum for a Hepatitus-B virus, presently requires in vivo inoculation of the suspect human serum into a chimpanzee, although many procedures are available to detect products of such a suspect viral deoxyribonucleic acid. The use of chimpanzees is costly and time consuming, whereas the detection of such products is indirect. The detection of other pathogenic agents present like problems of cost, unreliability, need for invasion sampling and the like.

OBJECTS OF THE INVENTION

It is an object of the present invention to provide a novel method for the detection of a viral DNA in an acellular biological fluid, such as human serum, cerebral spinal fluid or the like.

Another object of the present invention is to provide an efficacious method for the detection of a viral DNA in an acellular biological fluid, such as human serum, cerebral spinal fluid or the like obviating the clinical use of mammalian species.

A further object of the present invention is to provide a novel method for the detection of a viral DNA in an acellular biological fluid, such as human serum, cerebral spinal fluid or the like, more economical and reliable than present methods.

Still another object of the present invention is to provide a novel method for the detection of a viral DNA in an acellular biological fluid, such as human serum, cerebral spinal fluid or the like, permitting of substantially fast assay.

Yet another object of the present invention is to provide a novel method for the detection of a viral DNA in an acellular biological fluid, such as human serum, cerebral spinal fluid or the like, obviating the growth of the pathogen in vivo or in vitro.

SUMMARY OF THE INVENTION

These and other objects of the present invention are achieved by treating an acellular biological fluid, such as human serum, to immobilize in denatured form the deoxyribonucleic acids including the suspect viral deoxyribonucleic acid on a solid support or substrate and by contacting the solid support or substrate with radioisotopically-labeled viral denatured DNA to permit the radioisotopically-labeled DNA to renature to any immobilized suspect viral DNA. These steps are followed by analysis to detect radioisotopically-labeled suspect viral renatured DNA.

DETAILED DESCRIPTION OF THE INVENTION

A sample of an acellular biological fluid such as human serum, cerebral spinal fluid, urine or the like believed to contain a suspect virus-containing DNA, such as Hepatitis-B virus, Herpes Simplex Virus Type 1, Herpes Simplex Virus Type 2, cytomegalovirus, Epstein Barr virus, bacteria or the like, is mixed with a detergent, such as sodium dodecyl sulfate, and a proteolytic enzyme, such as Proteinase K (Boeringer, Mannheim) in an aqueous media. The mixture is maintained at a temperature in the range of from 60° to 80° C., preferably about 70° C., for a period of time in the range of 1 to 10 hours, preferably about two hours to facilitate the disruption of virus particles thereby ensuring high yields of DNA. The resulting solution is extracted with organic solvents, such as phenol and chloroform to extract into an organic phase most of the proteins thereby resulting in an aqueous phase containing substantially all of the DNA.

To the aqueous phase, there is added a base, such as sodium hydroxide, e.g. a solution of 1.0M sodium hydroxide to achieve a pH range of 10 to 12, preferably about 11.5 to effect denaturation of the DNAs. Thereafter, the solution is brought to a neutral pH by the addition of an acid, such as hydrochloric acid and a buffer, such as trishydroxyaminomethane to re-establish a pH of about 7.0. After achieving a neutral pH, the concentration of salt in the aqueous phase is increased through the inclusion, at high concentration of a salt, such as sodium chloride, a procedure to enhance binding of denatured DNAs, as more fully hereinafter discussed.

The aqueous solution of denatured DNAs including suspect viral denatured DNA is passed through or applied onto a solid substrate, such as a filter of commercially-available pure nitrocellulose, to effect immobilization of the denatured DNAs to the solid substrate. Application of the mixture to the solid substrate is advantageously effected by concomitant use of a gentle vacuum. After filtration, the solid substrate is baked under a vacuum at a temperature of from 60° to 100° C., preferably 75° C. for a time of from 1 to 6 hours, preferably 2 hours. The baked solid substrate is then treated to prevent further binding of nucleic acid to the solid substrate.

A quantity of purified recombinant DNA containing the sequence cording for the suspect viral genome is radioisotopically-labeled at high specific activity. Radioisotopes employable in this procedure include $P^{32}$, $I^{125}$, $I^{131}$ and $H^3$. The radioisotopically-labeled suspect viral recombinant DNA is denatured and applied onto the solid substrate containing the immobilized denatured DNAs for a predetermined time period and under chemical and thermal conditions sufficient to renature of hybridize any suspect viral denatured DNA immobilized on the solid substrate. Thus, the radiosotopically-labeled suspect viral denatured recombinant DNA (or probe) is caused to bind by hydrogen bonds with the complimentary sequence of the suspect viral denatured DNA bound to the solid substrate.

After a predetermined time period, the solid substrate is subjected to a washing procedure to remove non-specifically bound radioisotopically-labeled suspect viral denatured DNA. The solid substrate is then subjected to analysis to detect radioisotopically-labeled suspect viral renatured DNA, such as by scintillation spectrometry or autoradiography techniques. Any apparatus for such techniques may not only detect the radioisotopically-labeled suspect viral renatured DNA, but also quantitatively evaluate the viral population thereof.

The invention will further be described by the following example; however, the scope of the invention is not to be limited thereby.

EXAMPLE

In a 1.5 ml. test tube there is added 1 mg. of Proteinase K to 100 µl. of a mixture [100m sodium acetate pH 6.5,2% (w/v) sodium dodecylsulfate, 10m ethylenediaminotetracetic acid, 50 µg./ml. DNA from herring sperm, 100µug/ml. transfer RNA (from yeast)]. From a chronic carrier of Hepatitis-B,300 ml. of a serum sample is withdrawn and introduced into the test tube and incubated at 70° C. for one hour. 300 µl of phenol is added and admixed to form an emulsion. Thereafter 300 µl of chloroform is admixed and an organic phase separated by centrifugation. Another aliquot of 300 µl of chloroform is admixed to the inorganic phase and after centrifugation, 50 µl of the resulting aqueous phase is introduced into a well of a 96 well "microfilter" plate. 50 µl of 1.0M NaOH is added to the aqueous phase and incubated for 5 minutes at about 20° C. 100 µl of a solution 1.5M NaCl 0.5M HCl and 100 µl of a solution of 2.5M NaCl 1.0M trishydroxyaminomethane (pH 7.0) are added to the sample.

The resulting solution is filtered through a pure nitrocellulose filter (Millipore Corp.) under gentle vacuum to produce a 3.0 mm diameter spot. The sample is washed with solution of 6 × SSC, dried and baked at 80° C. for 2 hours at approximately 50 microns Hg. After baking, the filter is immersed in a solution of 6 × SSC, 0.2° polyvinylpyrrolidone 360 (Sigma), 0.2 bovine serum albumin (fraction V Armour), 0.2% Ficoll ® (Sigma) and 0.5 mg./ml. DNA from herring sperm and thereafter incubated at 65° C. for 10 hours.
®Pharmacia A radioactively-labeled denatured viral DNA is prepared from 2 µg of DNA representing a recombinant DNA plasmid consisting of Hepatitis-B viral DNA inserted into a plasmid cloning vehicle pBR322 as template for the "nick translation" reaction (Rigby et al) to yield a radioactively-labeled DNA having a specific activity of approximately $1 \times 10^8$ dpm per µg of DNA. The nitrocellulose filter is added to the renaturation mix including the radioactivity-labeled viral DNA and the filter heated to 85° C. for 10 minutes and quickly chilled. Renaturation is effected for 18 hours at 37° C. Following renaturation, the nitrocellulose filter is washed several times with a solution of 1.5M NaCl, 50 mM sodium phosphate buffer (pH 6.8), 10 µM ethylenediaminotetracetic acid and 0.5 w/v% sodium dodecylsulfate.

The nitrocellulose filter is placed between clear acetate films and disposed proximate an X-ray film. An intensifying screen is placed on the opposite side with the resulting laminate packaged to be light tight. After a predetermined period of time, the film is developed, with the presence of the viral DNA of Hepatitis-B being determined by the presence of a spot on the film.

The method of the present invention for the detection of a suspect viral DNA from acellular biological fluids includes a plurality of highly desirable processing steps other than the basic steps of denaturation, immobilization and renaturation to obtain the high degree of reliability or reproducibility. Thus, organic extraction permits removal of protein and the removal of detergent which could interfere with the binding of denatured DNAs to the solid substrate. Neutralization of the inorganic phase after denaturation of DNAs improves binding efficiency of denatured DNAs to the solid substrate. Baking adds to reliability as well as treatment of the nitrocellulose to prevent non-specific binding of DNA following baking. Washing of the solid substrate after renaturation also adds to reliability of results.

Numerous modifications and variations of the above-disclosed invention are possible in light of the above teaching and, therefore, within the scope of the appended claims the invention may be practiced otherwise than as particularly described.

What is claimed:

1. A method for evaluating an acellular biological fluid as drawn from a subject for the presence of a suspect viral DNA thereby obviating in vivo or tissue culture techniques, consisting essentially of:
   (a) treating said acellular biological fluid to immobilize on a solid substrate in denatured form said suspect viral DNA present in said acellular biological fluid;
   (b) contacting said solid substrate with a radioisotopically-labeled suspect viral denatured DNA probe to renature said immobilized suspect viral DNA present on said substrate to form a radioisotopically-labeled renatured DNA; and
   (c) evaluating the product of step (b) for the presence of said radioisotopically-labeled renatured DNA.

2. The method as defined in claim 1 wherein said acellular biological fluid is human serum.

3. The method as defined in claim 1 wherein said acellular biological fluid is cerebral spinal fluid.

4. The method as defined in claims 1 or 2 wherein said suspect viral DNA is DNA of the infectious agent Hepatitis-B.

5. The method as defined in claims 1 or 3 wherein said suspect viral DNA is Herpes Simplex Virus Type 1.

6. The method as defined in claims 1, 2 or 3 wherein said acellular biological fluid is treated with an organic solvent prior to step (a) to remove protein matter in an organic phase.

7. The method as defined in claim 6 wherein said evaluation of step (b) is effected by scintillation spectrometric technique.

8. The method as defined in claim 6 wherein said evaluation of step (c) is effected by autoradiographic technique.

9. The method as defined in claim 6 wherein said solid substrate is pure nitrocellulose.

10. The method as defined in claim 6 wherein step (a) includes the use of a slight vacuum to effect immobilization.

11. The method for evaluating an acellular biological fluid as drawn from a subject having normal DNA for the presence of a suspect viral DNA, consisting essentially of:
(a) contacting said acellular biological fluid with a detergent and proteolytic enzyme;
(b) extracting the product of step (a) with an organic solvent to form an essentially protein-free aqueous phase containing said normal DNA and suspect viral DNA present in said acellular biological fluid;
(c) contacting said aqueous phase of step (b) with an alkaline to denature said normal DNA and suspect viral DNA present in said acellular biological fluid;
(d) neutralizing the resulting solution of step (c);
(e) applying the solution of step d) to a solid substrate to immobilize said denatured normal DNA and suspect viral DNA present in said acellular biological fluid thereto;
(f) contacting said solid substrate of step (e) with a solution of radiolabeled suspect viral denatured DNA probe to renature said suspect viral denatured DNA present in said acellular biological fluid and immobilized on said solid substrate to form a radiolabeled suspect viral renatured DNA; and
(g) evaluating said solid substrate for said radiolabeled suspect viral renatured DNA.

12. The method as defined in claim 11 wherein step (a) is effected at a temperature of from 60° and 80° C. for a time period of from 1 to 10 hours.

13. The method as defined in claim 12 wherein temperature is 70° C. for a time period of 2 hours.

14. The method as defined in claim 11 wherein step (c) is effected at a pH of from 10 to 12.5.

15. The method as defined in claim 14 wherein said pH is 11.5.

16. The method as defined in claim 11 wherein said solid substrate of step (e) is baked at a temperature of from 60° to 100° C. for from 1 to 6 hours prior to step (f).

17. The method as defined in claim 11 or 16 wherein said solid substrate is treated to prevent further binding of nucleic acid thereto.

18. The method as defined in claim 11 wherein said solid substrate of step (f) is washed prior to step (g) to remove nonspecifically bound radiolabeled suspect viral denatured DNA.

19. The method as defined in claim 11 wherein step (g) is effected by scintillation spectrometry.

20. The method as defined in claim 11 wherein step (g) is effected by autoradiography.

* * * * *